(12) United States Patent
Schaefer

(10) Patent No.: US 11,998,920 B2
(45) Date of Patent: Jun. 4, 2024

(54) CONFIGURABLE DEVICE FOR THE FLEXIBLE PROVISION OF CONNECTIONS AND/OR FUNCTIONS IN A BIOPHARMACEUTICAL PROCESS

(71) Applicant: SARTORIUS STEDIM BIOTECH GMBH, Goettingen (DE)

(72) Inventor: Jan Schaefer, Goettingen (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 884 days.

(21) Appl. No.: 17/042,801

(22) PCT Filed: Mar. 13, 2019

(86) PCT No.: PCT/EP2019/056344
§ 371 (c)(1),
(2) Date: Sep. 28, 2020

(87) PCT Pub. No.: WO2019/185356
PCT Pub. Date: Oct. 3, 2019

(65) Prior Publication Data
US 2021/0023564 A1 Jan. 28, 2021

(30) Foreign Application Priority Data
Mar. 29, 2018 (DE) .................... 10 2018 107 679.7

(51) Int. Cl.
*B01L 3/00* (2006.01)
(52) U.S. Cl.
CPC .............. *B01L 3/561* (2013.01); *B01L 3/563* (2013.01); *B01L 3/565* (2013.01); *B01L 3/567* (2013.01);
(Continued)

(58) Field of Classification Search
CPC .......... B01L 3/561; B01L 3/563; B01L 3/565; B01L 3/567; B01L 2300/021;
(Continued)

(56) References Cited

U.S. PATENT DOCUMENTS 8,623,297 B2   1/2014 Le Comte et al.
9,192,934 B2   11/2015 Rensch et al.
(Continued)

FOREIGN PATENT DOCUMENTS

CN   101765775 A   6/2010
CN   104870628 A   8/2015
(Continued)

OTHER PUBLICATIONS

Flyer of the company GEMÜ, Gebr. Müller Apparatebau GmbH & Co. KG „Mehrweg-Ventilblöcke aus Kunststoff, Dec. 2017.
(Continued)

*Primary Examiner* — Jill A Warden
*Assistant Examiner* — John McGuirk
(74) *Attorney, Agent, or Firm* — Dilworth IP, LLC

(57) ABSTRACT

A configurable device for the flexible provision of connections and/or functions in a biopharmaceutical process includes a body in which predefined pipe sections and plug-in locations are formed by recesses in the material of the body. The configurable device further includes a plurality of functional elements which are adapted to be inserted into the plug-in locations.

24 Claims, 5 Drawing Sheets

(52) U.S. Cl.
CPC ... *B01L 2300/021* (2013.01); *B01L 2300/041* (2013.01); *B01L 2300/049* (2013.01); *B01L 2300/0627* (2013.01); *B01L 2300/0681* (2013.01); *B01L 2300/123* (2013.01); *B01L 2400/06* (2013.01)

(58) Field of Classification Search
CPC ......... B01L 2300/041; B01L 2300/049; B01L 2300/0627; B01L 2300/0681; B01L 2300/123; B01L 2400/06; C12M 37/02; C12M 37/04; C12M 37/06; C12M 23/42
See application file for complete search history.

(56) References Cited

U.S. PATENT DOCUMENTS

| | | | |
|---|---|---|---|
| 9,546,747 B2 | 1/2017 | Hofman | |
| 11,161,078 B2 | 11/2021 | Loewe et al. | |
| 2011/0124098 A1* | 5/2011 | Rose | B03C 5/026 435/306.1 |
| 2011/0189713 A1 | 8/2011 | Le Comte et al. | |
| 2014/0120010 A1 | 5/2014 | Rensch et al. | |
| 2017/0227525 A1 | 8/2017 | Griffith et al. | |
| 2017/0239661 A1 | 8/2017 | Berthier et al. | |
| 2018/0078936 A1* | 3/2018 | Owens | B01L 3/502715 |
| 2019/0083936 A1 | 3/2019 | Loewe et al. | |

FOREIGN PATENT DOCUMENTS

| | | | |
|---|---|---|---|
| CN | 107305989 A | 10/2017 | |
| DE | 102015114004 A1 | 3/2017 | |
| DE | 202017103082 U1 | 6/2017 | |
| EP | 2210666 A1 | 7/2010 | |
| EP | 2574789 A2 | 4/2013 | |
| WO | 2014042827 A2 | 3/2014 | |
| WO | WO-2015113582 A1 * | 8/2015 | ............. B01L 3/561 |
| WO | 2017032560 A1 | 3/2017 | |

OTHER PUBLICATIONS

International Search Report Issued in International Application No. PCT/EP2019/056344, Issued Jun. 27, 2019, 2 pages.

Hui, Ju, Progress in the On-Chip-Biofabrication technology, OME Information, No. 04, Apr. 2022, pp. 19-23, 25.

* cited by examiner

CONFIGURABLE DEVICE FOR THE FLEXIBLE PROVISION OF CONNECTIONS AND/OR FUNCTIONS IN A BIOPHARMACEUTICAL PROCESS

The invention relates to a configurable device for the flexible provision of connections and/or functions in a biopharmaceutical process in which primarily aqueous media are processed.

BACKGROUND OF THE INVENTION

For the manufacturers of biopharmaceutical products it becomes increasingly important to be able to adapt production capacities to market demand quickly and flexibly. In this context, single-use devices, which are arranged modularly in a process chain, are of an increasing significance. With such single-use devices, a high degree of flexibility as well as savings in time, investment and operating expenses can be achieved, in particular with regard to cleaning and inspection.

For carrying out specific unit operations in biopharmaceutical processes, prefabricated standardized device arrangements are often employed, which can be configured for versatile uses. An example of such a solution is the FlexAct® system by Sartorius Stedim Biotech GmbH, which is flexibly adaptable and can be made use of, inter alia, for buffer production, deep-bed filtration, virus inactivation, media preparation, virus depletion, or leak testing. The core of this device arrangement is a compact central multifunctional operating module in the form of a stainless steel trolley with a control unit and an operating panel. The FlexAct® system allows certain unit operations involving selected disposable process components (bags, hose lines, connectors, filter capsules, etc.) to be performed at least partly in an automated manner.

The device arrangements known from the prior art are subjected to certain restrictions. A device arrangement is usually designed for a particular process step involving a specific volume. An installation or conversion of the device arrangement on the part of the user can only be carried out with great effort, which results in an increased susceptibility to errors. In this context, particularly a fast and correct connection of single-use process components presents a challenge, since the required hose connections reach a high degree of complexity. In addition, attention has to be paid to maintaining the tightness of the sensitive connections, the pressure resistance of the piping and the sterility of the entire device. A further problem of existing systems is the lack of drainability.

SUMMARY OF THE INVENTION

It is the object of the invention to overcome the limitations of the device arrangements known from the prior art.

This object is achieved by a configurable device for the flexible provision of connections and/or functions in a biopharmaceutical process, including the features of claim 1. Advantageous and expedient further developments of the device according to the invention are indicated in the dependent claims.

The configurable device according to the invention for the flexible provision of connections and/or functions in a biopharmaceutical process comprises a body in which predefined pipe sections and plug-in locations are formed by recesses in the material of the body. The configurable device according to the invention further comprises a plurality of functional elements which are adapted to be inserted into the plug-in locations.

The invention is based, for one, on the finding that in order to avoid complex and susceptible hose connections between process components, a rigid, solid body can be used in which the necessary connections are formed by recesses in the material of the body. Such a body can be manufactured using modern production methods (injection molding, 3D printing or the like) from a material that can be sterilized for single use in a desired configuration.

The pipe sections within the body of the device according to the invention can be designed such that a pressure stability meeting the requirements for aqueous media is ensured. Depending on the thickness of the material of the body surrounding the pipe sections, pressures are even possible that would not be achievable at all or only at considerable additional expense when conventional hose lines are used. This is of particular significance for integrity tests, which are usually carried out at high pressures. While conventional process setups using hose lines can typically only be designed for a maximum pressure in the range of about 1 bar to 3 bars (with fabric-reinforced hoses), the device according to the invention allows much higher pressures, for example in the range of the nominal pressure levels PN 10 or PN 16 or even higher. Owing to the increased resistance to pressure, on the one hand, new areas of application can be opened up; on the other hand, this increases system safety since damage due to possible pressure shocks can be avoided.

In addition, the device according to the invention allows processes involving very large volumes to be carried out, since pipe sections having diameters of more than 1 inch (2.54 cm) can be provided within the body. Thus, the device according to the invention opens up new capacity ranges, because hoses having diameters that would be suitable for biopharmaceutical applications are not currently available.

The other essential aspect of the invention is the flexible equipping of the plug-in locations formed in the body of the device with functional elements. The functional elements allow a flow path to be established that is adapted to the respective requirements, including a direct incorporation of functions that are needed for the process to be carried out. This allows the manufacturer to keep a certain number of one or more standard body types in stock, which can then be individually configured by appropriately fitting them with functional elements. However, it is also possible to provide a special body with custom-made pipe sections and plug-in locations for a desired process. In any case, the selection and equipping of the body with functional elements can be performed by the manufacturer of the device in accordance with customer requirements prior to delivery of the device.

The equipping or fitting with functional elements can also be effected directly at the customer's site. In this case, the body of the device is supplied by the manufacturer in a standard or customized configuration to the customer, who will then carry out the placement of functional elements in accordance with the manufacturer's specifications or his or her own requirements. Here, the body pre-sterilized by the manufacturer can be equipped with sterile functional elements at the customer's site in a sterile environment. Alternatively, the customer may first equip the body with the functional elements in a non-sterile environment before sterilizing the entire equipped device. Basically, it is also possible for the customer to produce the body of the device himself/herself (in accordance with the manufacturer's specifications), in particular with the aid of a 3D printer.

A further essential advantage of the invention is the possibility to design the body with the predefined pipe sections and plug-in locations so as to be very compact, with short conduction paths and little to no dead space compared to conventional process setups. Also of particular advantage is the improved drainability of the body, which, unlike conventional setups, can be rotated as a whole in all spatial directions, so that in principle a complete "gravimetric" emptying is made possible, i.e. a complete draining of the body solely by virtue of the force of gravity acting on the aqueous medium inside the body. This is of great importance since the media passing through the process setup generally have a very high value.

In contrast to the hose connections which are complex in any case, defects (bursting), leaks and errors in connecting can be ruled out to the greatest possible extent. The direct incorporation of the functional elements into the flow path also contributes to the compactness, clarity and efficiency of the device.

The functional elements may, for one thing, be provided to prescribe specific flow courses within the body of the device. For example, a functional element can be used to establish a connection between two or more pipe sections adjacent to a plug-in location. For this purpose, the functional element may include at least one straight duct to connect two opposite pipe sections with each other, for example. Alternatively, the functional element may also include at least one curved or bent duct to provide a connection between two pipe sections that are not opposite each other. The functional element may also provide at least one pipe branching, e.g. in the form of a junction or an intersection, in order to combine fluid from a plurality of pipe sections and/or distribute fluid into a plurality of pipe sections.

In the event that no connection of two or more adjacent pipe sections is desired at a plug-in location, a functional element may be provided which blocks a connection between these pipe sections.

According to a particularly significant aspect of the invention, the individual functional elements—apart from establishing and/or blocking fluid connections—can be used to provide a large variety of functions that are relevant to carrying out a process. In particular, a functional element may be provided which includes a valve, in particular a switching valve (two-position valve) or a proportional valve. Likewise, a functional element may contain a sensor for detecting a process parameter. Process-relevant parameters that come into consideration include temperature, pressure, pH value, flow, conductivity, viscosity, turbidity, $CO_2$ content and interaction with UV radiation, for example.

Of particular advantage in this context is an embodiment in which the sensors are arranged "in-line", that is, they come into direct contact with the medium flowing through in the main flow path, thanks to the positioning of the functional elements in the plug-in locations adjacent to pipe sections. In comparison to "off-line" or "on-line" measurements (removal of a fluid sample from the flow path before a measurement with or without subsequent return into the flow path), a direct "in-line" measurement immediately provides unadulterated results that can be directly utilized in the open-loop or closed-loop process control.

The functional elements can also be used to provide hardware components of the process setup—or at least parts thereof. For example, a functional element may include a pump, a filter means, a chromatographic separator (chromatography column) or a membrane adsorber or essential parts thereof.

The body of the device according to the invention preferably already has connections formed thereon, which open into pipe sections in the interior of the body. In particular, commercially available sterile connectors are suitable for use as connections, allowing the device to be connected to external components in a simple manner.

The plug-in locations for the functional elements are preferably accessible via insertion openings on the surface of the body of the device.

According to a preferred embodiment, at least some of the insertion openings are formed in a top surface of the body. This has the advantage of an especially easy handling since the functional elements can be conveniently inserted from top to bottom. In addition, a simple view onto the body from above allows the user to see immediately and clearly which plug-in locations are occupied by functional elements. If the functional elements are appropriately marked, it is furthermore possible to see at a glance which functional elements have been inserted. In the case of functional elements with electrical signal and/or control lines and/or other lines, there is the additional advantage that all lines are led out of the device in the same direction.

The maximum possible flexibility in equipping the device according to the invention with functional elements is achieved by an embodiment in which the insertion openings and the plug-in locations are substantially equally shaped and dimensioned, and in which with regard to their cross-sectional shapes and dimensions, the functional elements are adapted to the insertion openings and the plug-in locations such that each functional element can be inserted into any desired plug-in location.

The "inner workings" of the body of the device according to the invention can basically be freely designed with respect to the arrangement of the pipe sections and plug-in locations. A clearly laid out structure is obtained in that pipe sections are arranged at different levels in the body.

Matched with such a structure, it is possible to use functional elements having a plurality of functional sections. In particular, a functional element may be employed which includes at least a first functional section and a second functional section, the first functional section cooperating with pipe sections of a first level and the second functional section cooperating with pipe sections of a second level. This means that by using only one functional element, a plurality of functions can be provided on different levels of the body. Here, the functional sections of the functional element may each provide the same function or different functions.

In order to ensure that a functional element is inserted correctly, a positioning means may be provided, which allows a complete insertion of a functional element only in one predefined orientation. In this way, errors in the fitting of the device according to the invention are effectively avoided. Tongue-and-groove systems or other poka-yoke measures are suitable as positioning means, for example.

The functional elements are preferably formed to have an electronic display or a permanent labeling or a symbol on the upper side. This provides a simple indication to the manufacturer or user of the device according to the invention which type of functional element has been inserted in the respective plug-in location.

For a design of the device according to the invention for a desired process volume or a desired pressure, an embodiment is advantageous in which the pipe sections within the body have a defined diameter, preferably all have the same diameter.

In view of the requirement mentioned at the outset for a fast and flexible adaptation of production capacities, the device according to the invention is intended to be employed primarily as a disposable device. In order to enable the customer to put the device into operation immediately after delivery, it is desirable for the device to be pre-sterilized at the manufacturer's already before delivery. To make this possible, the body is formed from a sterilizable plastic material, and the functional elements are preferably also sterilizable. This allows the entire device to be delivered in the preconfigured state, i.e. with functional elements already inserted, with the device pre-sterilized, ready for connection and operation.

BRIEF DESCRIPTION OF THE DRAWINGS

Further features and advantages of the invention will be apparent from the following description and from the accompanying drawings, to which reference is made and in which.

DETAILED DESCRIPTION OF THE INVENTION

Figure 1:
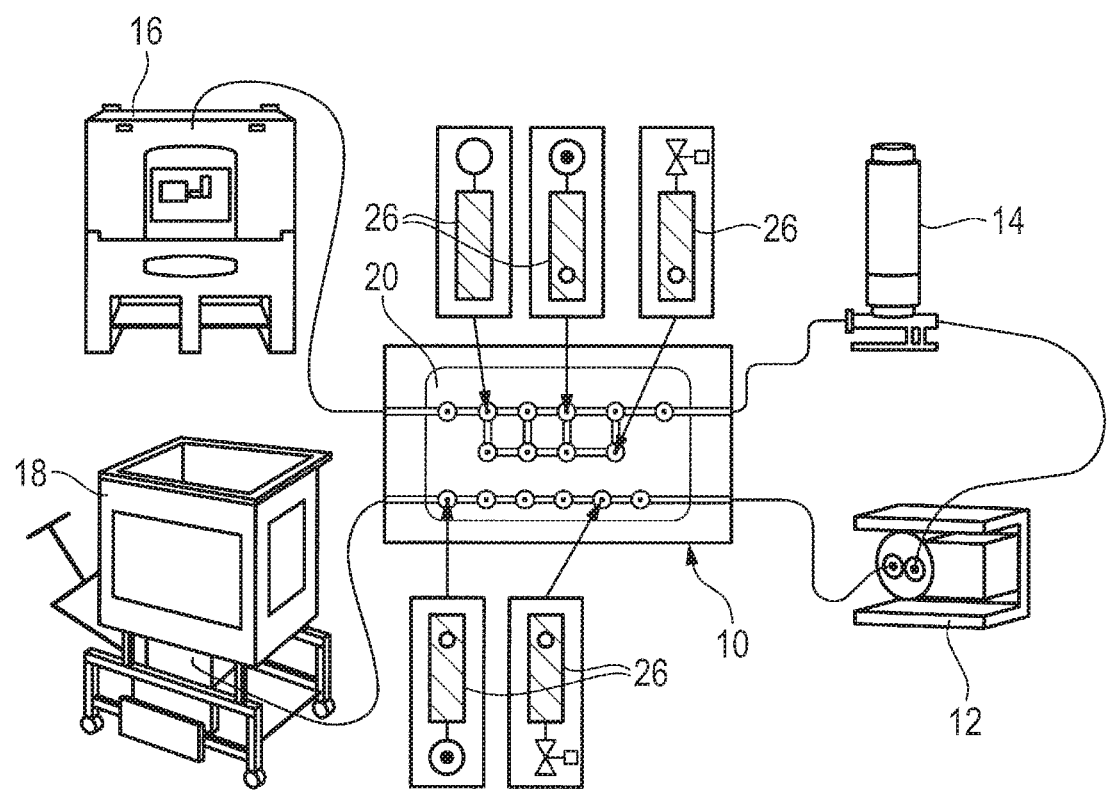
FIG. 1 shows a schematic view of a configurable device according to the invention in a process environment.

FIG. 1 illustrates, by way of example, a configurable disposable device 10 for a flexible provision of connections and functions in a biopharmaceutical process environment. The process environment here includes a pump 12, a filtration device with a filter capsule 14, a standard disposable container 16, and a standard disposable container with a mixing unit 18.

The configurable device 10 is used, for one thing, to provide the fluidic connections, required for the process to be carried out, between the components of the process environment such that the components only need to be connected to given connections of the device 10 in a simple manner using simple hose lines. For another thing, the configurable device 10 itself provides specific process functions.

Figure 2:
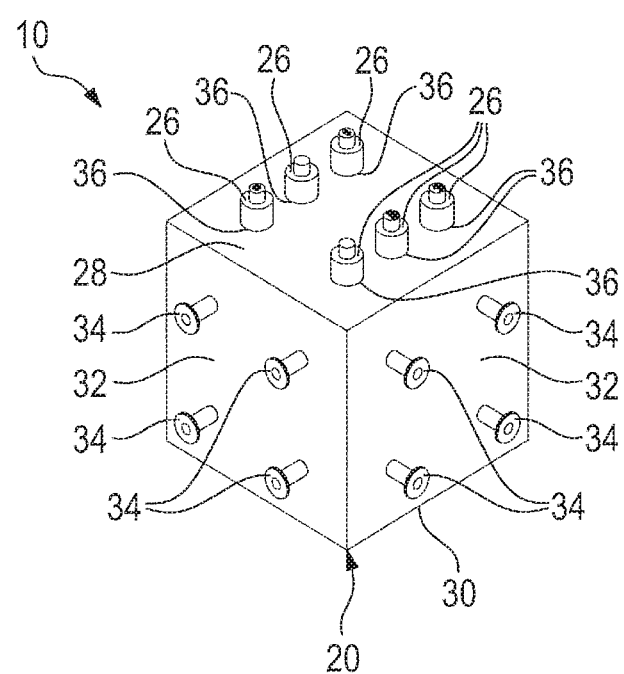
FIG. 2 shows a perspective view of another embodiment of a device according to the invention with functional elements inserted.
Figure 3:
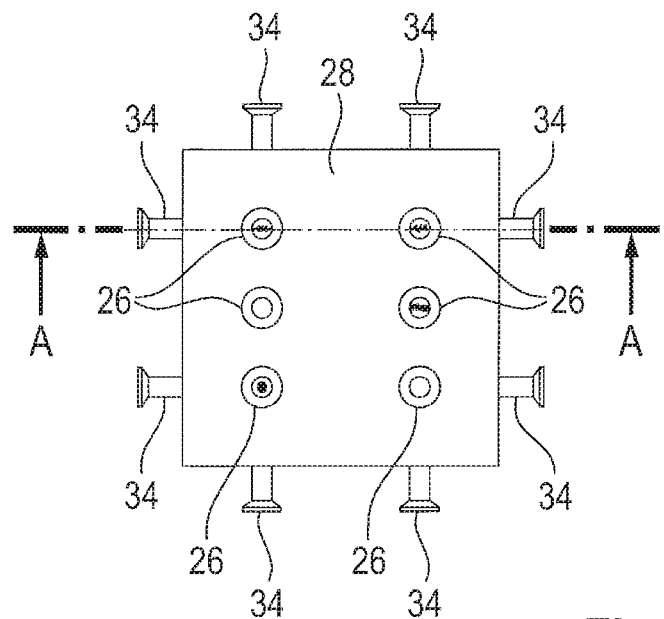
FIG. 3 shows a top view of the device from FIG. 2.
Figure 4:
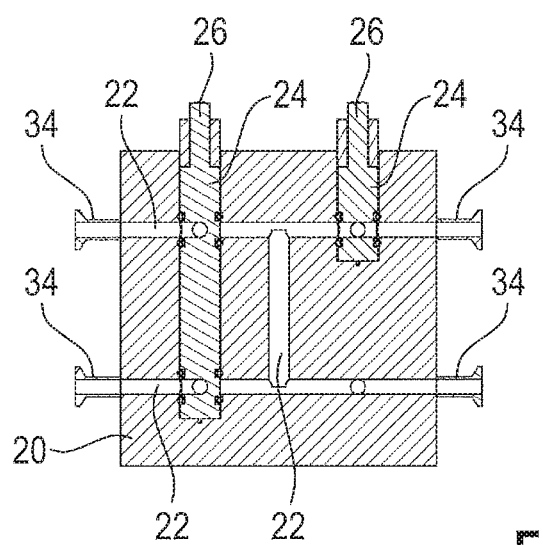
FIG. 4 shows a sectional view along the section line A-A from FIG. 3.

The structure and the mode of operation of the configurable device 10 will be discussed below on the basis of an exemplary embodiment which should in no way be understood in a limiting sense and which is shown in FIGS. 2, 3 and 4.

The device 10 essentially consists of a preferably solid plastic body 20, in which a plurality of permanently pre-defined pipe sections 22 and plug-in locations 24 for insertable functional elements 26 are formed. The pipe sections 22 and the plug-in locations 24 are essentially formed by recesses in the material of the body 20.

The body 20 here has a cubic basic shape with a top surface 28, a bottom surface 30 and side surfaces 32. The side surfaces 32 have a plurality of connections 34 formed thereon, which open into pipe sections 22 in the interior of the body 20. As is apparent from FIGS. 2, 3 and 4, the connections 34 and the pipe sections 22 are arranged in two levels.

The plug-in locations 24 of the configurable device 10 are accessible via insertion openings 36 in the top surface 28 of the body 20. A functional element 26 can be inserted into each plug-in location 24. Basically, however, it is also possible to leave plug-in locations 24 free. The insertion openings 36 for the plug-in locations 24 are preferably all of the same shape and dimensions. Different types of functional elements 26 are provided, which, however, are preferably all adapted to the insertion openings 36 and the plug-in locations with regard to their cross-sectional shapes and dimensions such that each functional element 26 can basically be introduced into any of the insertion openings 36 and received in the associated plug-in location 24.

Figure 5:
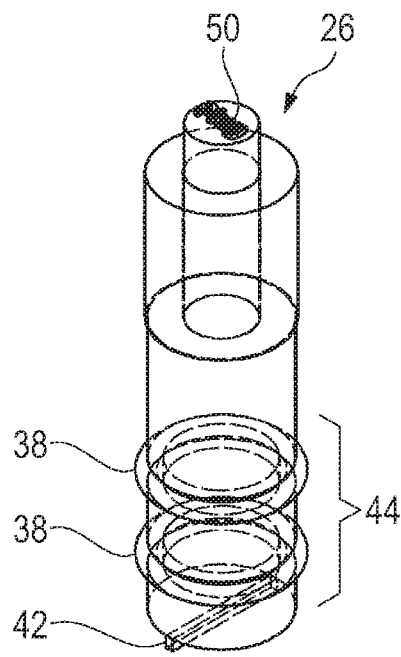
FIG. 5 shows a perspective transparent view of a first functional element for use in the device according to the invention.

In its simplest form, a functional element 26, when in its inserted state, can block the connection between two or more pipe sections 22 adjacent to the plug-in location 24. An example of such a functional element 26 in the form of a plug is shown in FIG. 5. Seals make sure that the plug-in location 24 is sealed off from the pipe sections 22 that open into it, the seals being in the form of two O-rings 38 here which, in the inserted state of the plug, are arranged above and below the pipe sections 22.

Figure 6:
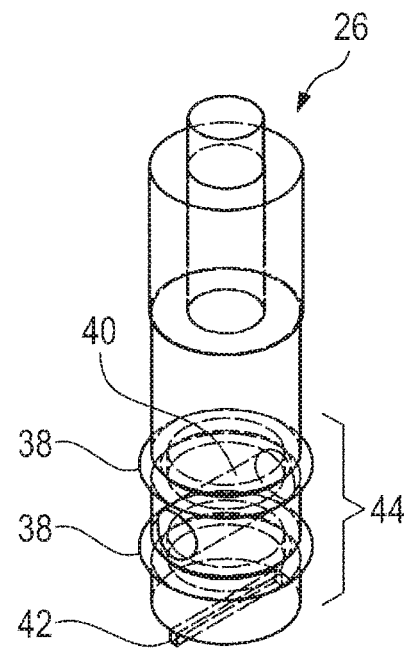
FIG. 6 shows a perspective transparent view of a second functional element.

FIG. 6 shows a different functional element 26, which can be used to establish a fluid communication between two opposite pipe sections 22 in the same level ("2 ways"). To this end, a straight duct 40 is formed between the O-rings 38 in the functional element 26.

A positioning means here provides for a correct orientation of the duct 40 when the functional element 26 is in its inserted state—as is also the case with other functional elements 26 for which a correct orientation is required for providing the function. This positioning means may take the form of an oblong web 42 on the lower side of the functional element 26, as shown here as an example. The web 42 is matched with a corresponding groove of the plug-in locations 24 in the nature of a tongue-and-groove connection, so that in the correct installation state, an anti-rotation device for the functional element 26 is formed in the plug-in location 24. However, other positioning means are also possible.

Figure 7:
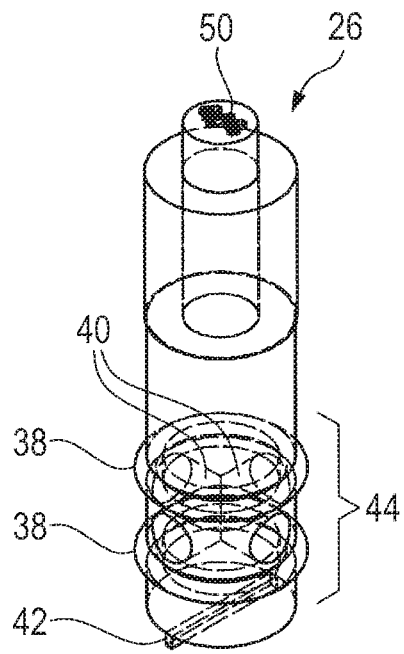
FIG. 7 shows a perspective transparent view of a third functional element.

A further example of a functional element 26 is shown in FIG. 7. Here, a pipe branching in the form of two intersecting ducts 40 is formed ("4 ways").

The functional elements 26 shown in FIGS. 5 to 7 are dimensioned such that when in the inserted state, they cooperate with the pipe sections 22 of the upper level.

Figure 10:
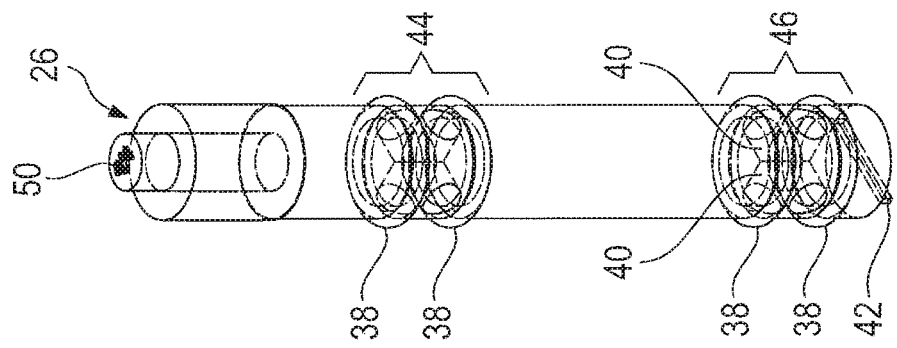
FIG. 10 shows a perspective transparent view of a sixth functional element.
Figure 9:
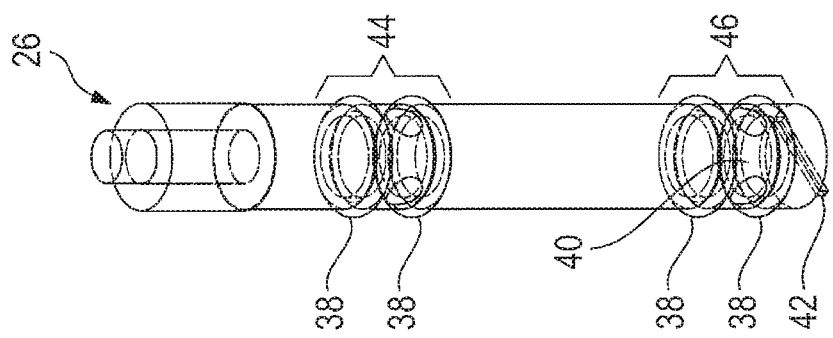
FIG. 9 shows a perspective transparent view of a fifth functional element.
Figure 8:
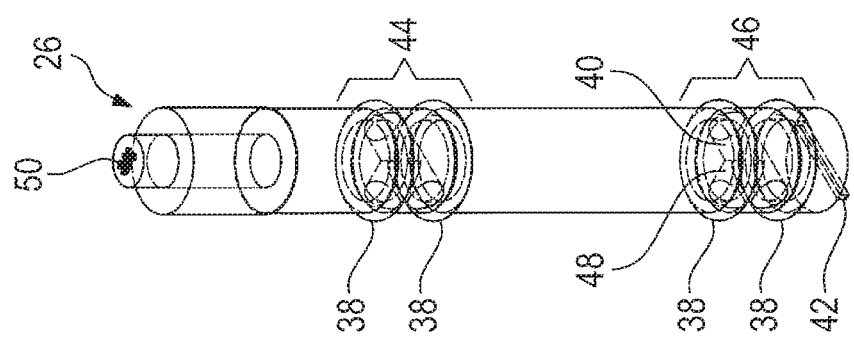
FIG. 8 shows a perspective transparent view of a fourth functional element.

FIGS. 8 to 9 show functional elements 26 which each fulfill two functions. In the inserted state, a first functional section 44 cooperates with the pipe sections 22 of the upper level and a second functional section 46 cooperates with the pipe sections 22 of the lower level. The functional element 26 of FIG. 8 has a duct 40 with a branch connection 48 ("3 ways") in both functional sections 44, 46. The functional element 26 shown in FIG. 9 has a curved duct 40 (bend) in both functional sections 44, 46. The functional element 26 of FIG. 10 has a pipe branching in the form of two intersecting ducts 40 ("4 ways") in both functional sections 44, 46.

A functional element 26 may basically include one, two or even more than two functional sections 44, 46. It is also possible for the functional sections 44, 46 of a functional element 26 to have different functions realized therein. The functions are also not limited to the blocking or connecting of pipe sections 22 in the body 20. Rather, the functional elements 26 may contain, for example, a valve (switching or proportional valve) and/or a sensor for sensing temperature, pressure, pH value, flow, conductivity, viscosity and/or other process-relevant parameters. Pumps, filter devices and other hardware components provided for carrying out the process can also basically be realized. A functional element 26 may also contain only part of a hardware component, for example specific parts of a pump or of a valve, which are designed for single use and are sterilizable. In this case, the other part of the functional component, for example a drive, is located outside the device 10 and is connected in a suitable manner (electrically, mechanically, hydraulically, pneumatically, . . . ) to the part received in the functional element 26. For this purpose, appropriate lines are provided, which are led through on the upper side of the functional element 26. Such lines, in particular signal and/or control lines, may also be provided if the functional element 26 is connected to another component of the process setup outside the body 20.

On their upper sides, the functional elements 26 each carry an electronic display 50 or permanent letterings and/or symbols that provide information on the functions implemented in the functional sections 44, 46.

The body 20 of the configurable device 10 may, of course, include less or more than two levels with connections 34 and pipe sections 22. The connections 34, pipe branches 22 and plug-in locations 24 need not necessarily be arranged in defined levels either. Furthermore, provision may be made that the insertion openings 36 for the functional elements 26 are provided on different surfaces of the body 20, so that the functional elements 26 are inserted into the body 20 in different directions.

Owing to the selectable equipping with functional elements 26, the device 10 can be used to implement different process setups with individually configurable flow paths and components, with the functional elements 26, in particular the sensors, as "in-line" components, intentionally coming into direct contact with the fluid flowing through the pipe sections 22.

The pipe sections 22 in the body 20 have a predetermined, defined diameter and are sturdy enough to reliably withstand a predefined maximum pressure. This maximum pressure is primarily determined by the diameter of the pipe sections 22 and the thickness of the material surrounding them.

The body 20 of the configurable device 10 is made from a sterilizable plastic material, for example using an injection molding method or with the aid of a 3D printer. The body 20 may be provided as a one-piece block or assembled from a plurality of individual parts, in particular by adhesive bonding or ultrasonic welding.

The body 10 with the connections 34 and the pipe branches 22 as well as the functional elements 26 can be sterilized both individually and as a ready-configured device 10 with functional elements 26 already inserted, if appropriate even in a packaged state, so that the entire configured device 10 can be delivered to the customer ready for connection and operation. But it is also possible for the customer to equip the body 20 with the functional elements 26, in which case the sterilization can take place before or after the equipping process. If applicable, the customer may also produce the body 20 himself/herself in accordance with the manufacturer's specifications.

LIST OF REFERENCE NUMBERS 10 configurable device
12 pump
14 filter capsule
16 disposable container
18 disposable container with mixing unit
20 body
22 pipe section
24 plug-in location
26 functional element
28 top surface
30 bottom surface
32 side surface
34 connection
36 insertion opening
38 O-ring
40 duct
42 web
44 first functional section
46 second functional section
48 branch connection
50 display

The invention claimed is:

1. A configurable device for flexible provision of connections and/or functions in a biopharmaceutical process, comprising a body in which predefined pipe sections and plug-in locations are formed by recesses in a material of the body, and comprising a plurality of functional elements which are adapted to be inserted into the plug-in locations to perform fluidic functions in the device, wherein one of the functional elements includes at least one duct that establishes a connection between two or more of the pipe sections in the body that open into one of the plug-in locations.

2. The configurable device according to claim 1, wherein the at least one duct is a straight duct.

3. The configurable device according to claim 1, wherein the at least one duct is a curved or bent duct.

4. The configurable device according to claim 1, wherein the one of the functional elements provides at least one pipe branching.

5. The configurable device according to claim 1, wherein another or the same one of the functional elements includes a valve.

6. The configurable device according to claim 1, wherein another or the same one of the functional elements includes a sensor for detecting a process parameter.

7. The configurable device according to claim 6, wherein the sensor of the another or the same one of the functional elements is arranged in a flow path and comes into direct contact with a medium flowing through.

8. The configurable device according to claim 1, wherein another or the same one of the functional elements includes a pump or parts of a pump.

9. The configurable device according to claim 1, wherein another or the same one of the functional elements includes a filter means, a chromatographic separator, a membrane adsorber or parts thereof.

10. The configurable device according to claim 1, characterized in that the body has connections formed thereon which open into pipe sections in an interior of the body.

11. The configurable device according to claim 1, characterized in that the plug-in locations are accessible via insertion openings on a surface of the body.

12. The configurable device according to claim 11, characterized in that at least some of the insertion openings are formed in a top surface of the body.

13. The configurable device according to claim 11, characterized in that the insertion openings and the plug-in locations are substantially equally shaped and dimensioned.

14. The configurable device according to claim 13, characterized in that, with regard to their cross-sectional shapes and dimensions, the plurality of functional elements are adapted to the insertion openings and the plug-in locations such that each functional element can be inserted into any plug-in location.

15. The configurable device according to claim 1, characterized in that pipe sections are arranged at different levels in the body.

16. The configurable device according to claim 15, characterized by at least one functional element that includes at least a first functional section and a second functional section, the first functional section cooperating with pipe sections of a first level and the second functional section cooperating with pipe sections of a second level.

17. The configurable device according to claim 16, characterized in that the first and second functional sections each provide a same function.

18. The configurable device according to claim 16, characterized in that the first and second functional sections provide different functions.

19. The configurable device according to claim 1, characterized in that a positioning means is provided which allows another or the same one of the functional elements to be fully inserted only in one predefined orientation.

20. The configurable device according to claim 1, wherein the plurality of functional elements have an electronic display or a permanent labeling or a symbol on an upper side.

21. The configurable device according to claim 1, wherein the pipe sections have a defined diameter.

22. The configurable device according to claim 1, wherein the body is formed of a sterilizable plastic material.

23. The configurable device according to claim 1, wherein the plurality of functional elements are sterilizable.

24. A configurable device for flexible provision of connections and/or functions in a biopharmaceutical process, comprising a body in which predefined pipe sections and plug-in locations are formed by recesses in a material of the body, and comprising a plurality of functional elements which are adapted to be inserted into the plug-in locations to perform fluidic functions in the device, wherein one of the functional elements includes a plug that blocks a connection between two or more of the pipe sections in the body that open into one of the plug-in locations.

\* \* \* \* \*